United States Patent [19]

Farina et al.

[11] Patent Number: 5,405,862
[45] Date of Patent: Apr. 11, 1995

[54] LOW FREE FORMALDEHYDE METHYLOLHYDANTOIN COMPOSITIONS

[75] Inventors: Thomas E. Farina, Flemington; Marvin Rosen, Wayne, both of N.J.

[73] Assignee: Lonza Inc., Fair Lawn, N.J.

[21] Appl. No.: 196,894

[22] Filed: Feb. 14, 1994

Related U.S. Application Data

[63] Continuation of Ser. No. 887,280, May 21, 1992, abandoned.

[51] Int. Cl.$^6$ .................... A01N 43/52; C07D 235/12
[52] U.S. Cl. .................. 514/389; 548/308.1; 548/312.1; 548/317.1; 548/319.1; 252/367; 252/368
[58] Field of Search ...... 514/389; 548/308.1, 548/312.1, 319.1, 317.1; 252/367, 368

[56] References Cited

U.S. PATENT DOCUMENTS

| | | | |
|---|---|---|---|
| 3,987,184 | 10/1976 | Foelsch | 548/312 |
| 4,908,456 | 3/1990 | Farina et al. | 548/312 |
| 5,036,095 | 6/1991 | Andermann | 514/389 |

Primary Examiner—Mary C. Lee
Assistant Examiner—Jacqueline Haley
Attorney, Agent, or Firm—Darby & Darby

[57] ABSTRACT

Compositions of dimethyloldimethylhydantoin, monomethyloldimethylhydantoin, and dimethylhydantoin having less than 0.1% by weight of free formaldehyde based upon 100% by weight of total composition; and wherein the weight ratio of dimethyloldimethylhydantoin to monomethyloldimethylhydantoin ranges from about 1:1.25 to about 3.5:1, are provided. These compositions may be prepared (1) by reacting dimethylhydantoin and a formaldehyde-containing source wherein the molar ratio of formaldehyde to dimethylhydantoin ranges from about 1.2:1 to about 1.55:1 or (2) by admixing (a) from about 80 to about 90% by weight of an aqueous solution of methyloldimethylhydantoin having greater than about 0.1% by weight of free formaldehyde with (b) about 20 to about 10% by weight of dimethylhydantoin based upon 100% weight of aqueous dimethyloldimethylhydantoin solution and dimethylhydantoin combined.

12 Claims, No Drawings

LOW FREE FORMALDEHYDE METHYLOLHYDANTOIN COMPOSITIONS

This is a continuation of application Ser. No. 07/887,280, filed May 21, 1992, abandoned.

FIELD OF THE INVENTION

This invention relates to the preparation of compositions comprising dimethyloldimethylhydantoin (DMDMH), monomethyloldimethylhydantoin (MDMH), and dimethylhydantoin (DMH) having less than 0.1% by weight of free formaldehyde based upon 100% by weight of total solution; wherein the weight ratio of DMDMH:MDMH ranges from about 1:1.25 to about 3.5:1. The compositions prepared according to the present invention are expected to meet and to surpass anticipated government formaldehyde content guidelines and to avoid other disadvantages of relatively high free formaldehyde content methylolhydantoin solutions, including unpleasant odor, skin irritation, loss of the volatiles of formaldehyde, and health hazards to production workers.

BACKGROUND OF THE INVENTION

Formaldehyde is a well-known antimicrobial agent that has been used widely to extend the shelf life of certain preparations that are susceptible to microbial growth. These preparations may include industrial products such as liquid detergents, water-based surfactants, soft soaps, water-based paints, fabric softeners, room deodorizers/air fresheners, polymer emulsions, protective coatings for textiles, architectural coatings, water-based gels, sealants and caulks, latexes for paper coatings, water-based inks, wood preservatives, etc. They may also include personal care products such as cosmetics, shampoos, creams, lotions, powder products, etc.

However, formaldehyde, particularly in high concentrations, has many disadvantages, such as an unpleasant odor, a propensity to irritate skin, and a short shelf life due to its high volatility. More importantly, formaldehyde has come under increasingly greater scrutiny by the medical community and by regulatory agencies due to its potential as a health risk.

DMDMH is a formaldehyde donor which releases formaldehyde slowly over a relatively long period of time and is typically produced by methylolating one mole of DMH with two moles of formaldehyde. MDMH, another formaldehyde donor, is prepared also by the methylolation using one mole of formaldehyde.

Foelsch, U.S. Pat. No. 3,987,184, discloses a method for the production of DMDMH which involves reacting 1.85 to 2.4 moles of formaldehyde per mole of 5,5-DMH in water, at a pH of from about 7 to about 9, for a period of about 20 minutes, at a temperature of about 22° to 65° C. Foelsch hypothesized that DMDMH solutions prepared in this manner would have under 1% by weight of free formaldehyde, but he exemplified only solutions having 1.2% by weight of free formaldehyde.

Alternative methods for achieving low free formaldehyde in DMDMH solutions have included the addition of ammonium carbonate to DMDMH solutions or the vacuum stripping of residual free formaldehyde from DMDMH solutions. These attempts have been unsuccessful in lowering free formaldehyde content below 0.1% by weight, however.

SUMMARY OF THE INVENTION

A direct reaction method and a post addition method have now been discovered which result in compositions of dimethyloldimethylhydantoin, monomethyloldimethylhydantoin, and dimethylhydantoin having less than 0.1% by weight of free formaldehyde based upon 100% by weight of total composition, wherein the weight ratio DMDMH to MDMH ranges from about 1:1.25 to about 3.5:1. Compositions described above are produced which overcome many of the disadvantages of the prior art and which comply with anticipated stringent regulatory agency requirements.

According to the present invention, there is provided a method (the direct reaction method) for producing these compositions comprising reacting dimethylhydantoin and a formaldehyde-containing source wherein the molar ratio of formaldehyde to dimethylhydantoin ranges from about 1.2:1, and preferably 1.3:1, to about 1.55:1. A most preferred ratio is about 1.35:1.

In a further embodiment (the post addition method), an aqueous solution of dimethyloldimethylhydantoin, monomethyloldimethylhydantoin, and dimethylhydantoin is produced by admixing (a) from about 80 to about 90% by weight of an aqueous solution of methylolated dimethylhydantoins having greater than 0.1% by weight of free formaldehyde with (b) about 20 to about 10% by weight of dimethylhydantoin based upon 100% by weight of aqueous solution of methylolated dimethylhydantoins and dimethylhydantoin combined.

Also contemplated by the invention are compositions comprising dimethyloldimethylhydantoin, monomethyloldimethylhydantoin, and dimethylhydantoin having less than 0.1% by weight of free formaldehyde based upon 100% by weight of the composition; wherein the weight ratio of DMDMH to MDMH ranges from about 1:1.25 to about 3.5:1. Preferred compositions have from about 10 to about 25% by weight of total formaldehyde and from about 2 to about 6% by weight of dimethylhydantoin based upon 100% by weight of the composition. Preferred compositions are aqueous solutions and most preferably are stable as explained below.

These compositions are used in biocidal effective amounts in any medium in which microbial growth is to be retarded, and particularly in industrial or personal care products.

DETAILED DESCRIPTION OF THE INVENTION

DMDMH is a formaldehyde donor which is the diformylated product of DMH and formaldehyde. MDMH is first formed as an intermediate, which itself is a formaldehyde scavenger containing about 19% by weight of bound, but available, formaldehyde. Subsequent reaction of MDMH with formaldehyde yields DMDMH which theoretically contains 31.9% of bound, but available, formaldehyde. DMDMH is typically found commercially in aqueous solutions containing at least 1% by weight of free formaldehyde based upon 100% by weight of total DMDMH solution.

The Direct Reaction Method

The direct reaction method of the present invention involves reacting dimethylhydantoin and a formaldehyde containing source wherein the molar ratio of formaldehyde to dimethylhydantoin ranges from about 1.2:1 to about 1.55:1 and preferably from about 1.3:1 to about 1.55:1. Most preferably, the molar ratio is about 1.35:1.

The formaldehyde containing source suitable for use herein may be any known to one of ordinary skill in the art including, but not limited to, aqueous solutions of formaldehyde such as formalin or substantially anhydrous formaldehyde such as paraformaldehyde. Preferably, the formaldehyde containing source comprises from about 36 to about 38% by weight of formaldehyde based upon 100% by weight of aqueous formaldehyde solution or about 95% by weight of formaldehyde based upon 100% by weight of paraformaldehyde. Preferably, the pH of the aqueous formaldehyde solution ranges from 8.1 to 8.3 at the beginning of the reaction.

The compositions prepared by the direct reaction method can be prepared either as aqueous solutions or as substantially anhydrous compositions, i.e., less than 1% by weight of water. Additionally, these substantially anhydrous forms can be diluted to yield aqueous solutions.

In a preferred embodiment, the direct reaction method includes the use of an aqueous solution of formaldehyde having a pH of from 8.2 to about 8.3, adjusting the pH of the initial dimethylhydantoin/aqueous formaldehyde solution reaction product to about 7, heating the pH adjusted product to a temperature ranging from about 45° C. to about 55° C. for a period of about 2½ to 3½ hours, cooling the heated product to about room temperature, and finally adjusting the pH to range of from about 6.2 to about 7.2.

The Post Addition Method

The post addition method involves the admixing of from about 80 to about 90% by weight, preferably from about 83 to about 90% by weight, and most preferably about 85% by weight of an aqueous solution of methyloldimethylhydantoins having greater than 0.1% by weight of free formaldehyde with correspondingly from about 20 to about 10% by weight, preferably about 17 to about 10% by weight, and most preferably about 15% by weight of dimethylhydantoin. Preferably, the aqueous solution of dimethyloldimethylhydantoin has from about 10 to about 18% by weight of total formaldehyde and/or from about 25% to about 60% by weight of dimethyloldimethylhydantoin.

The post addition method of the present invention reduces the amount of free formaldehyde in DMDMH solutions prepared by any method. However, this method is not as well suited for commercial use as is the direct reaction method because the post addition method requires greater quantities of DMH than the direct reaction method. Additionally, post addition increases the solids content of the resultant stable, low free formaldehyde composition, and increased solids content can lead to undesirable crystallization of the product.

The compositions prepared by direct reaction or by post addition preferably have from about 10% to 25% by weight of total formaldehyde based upon 100% by weight of the total composition. Most preferably, total formaldehyde ranges from about 12 to about 17% by weight. In particular preferred embodiments, the total formaldehyde content is either 12% or 17% by weight. Preferably, the compositions of the present invention will have a pH ranging from about 6.5 to 7.5, but the pH can be adjusted according to need with aqueous sodium hydroxide or the like.

Preferred DMDMH/MDMH/DMH compositions of the present invention comprise from about 20 to about 40% by weight of dimethyloldimethylhydantoin based upon 100% by weight of composition. Most preferably, they comprise from about 25 to about 35% by weight of dimethyloldimethylhydantoin. Furthermore, preferred low free formaldehyde DMDMH/MDMH/DMH compositions comprise from about 2 to about 6% by weight of dimethylhydantoin based upon 100% by weight of composition.

Stability is defined as maintenance of less than 0.1% by weight of free formaldehyde for at least 30 days and preferably for at least six months.

Mixing of components and addition of components in the methods of the present invention can be accomplished by conventional means known to those of ordinary skill in the art.

A second post addition can be used as an adjunct to the direct reaction method as described herein, and in fact for any out-of-spec batches prepared by the present methods or other methods. Preferably in this type of post addition, DMH will be added to aqueous DMDMH/MDMH/DMH solutions at an amount of from about 1 to 10% by weight and preferably from about 1 to about 3% by weight based upon 100% by weight of total DMDMH/MDMH/DMH solution.

DESCRIPTION OF THE PREFERRED EMBODIMENTS

The following examples illustrate the invention without limitation. All parts and percentages are given by weight unless otherwise indicated.

The following analytical methods were used. Free formaldehyde was determined by reaction with hydroxylamine hydrochloride. Each mole of formaldehyde liberates one mole of hydrogen chloride. The latter is determined potentiometrically by titration with alkali.

Carbon-13 NMR was used to determine composition (percentage of DMH, MDMH, and DMDMH) in the solutions.

Total formaldehyde was measured by one of two techniques. The first is the Hantzsch method where combined formaldehyde is liberated from the dimethylhydantoin ring by reaction with ammonium acetate and acetylacetone. Combined and free formaldehyde react with the latter two reagents to form 3,5-diacetyl-1,4-dihydrolutidine. The absorbance of the lutidine derivative is measured at 413 nanometers, and the formaldehyde is quantified by comparing to a calibration curve. The second means for measuring total formaldehyde is by alkaline oxidation. Formaldehyde is oxidized with hydrogen peroxide in a solution containing excess potassium hydroxide to form potassium formate. Excess potassium hydroxide is titrated potentiometrically with mineral acid.

Water was measured by the Karl Fischer technique.

The Direct Reaction Method

EXAMPLE 1

A 12 liter 3-necked round bottom flask equipped with a stirrer, a temperature regulator (Thermowatch TM and heating mantle), and a condenser was charged with 3133 grams of formalin (37% aqueous formaldehyde, 1.2% methanol) (39 moles formaldehyde) and 2163 grams of water. The pH was adjusted to 8.3 using aqueous sodium hydroxide. 3704 grams (29 moles) of DMH were added at room temperature in a molar ratio of formaldehyde to DMH of 1.35:1. An exotherm was observed, and the temperature increased to 31° C. After most of the DMH dissolved, the maximum temperature was reached, and the exotherm stopped. The pH was adjusted with aqueous sodium hydroxide to 7. The reaction was heated at 55° C. for three hours and was then cooled to room temperature. The pH was then adjusted to a range of from 6.8 to 7.5. 5 grams of filter aid (diatomaceous earth) were added, and the product was filtered. The product was then analyzed again.

The product was then stored for six months at 25° C. and subsequently analyzed again.

These procedures were repeated four additional times with similar results.

Representative properties are summarized in Table 1.

COMPARATIVE EXAMPLE 1A

An aqueous DMDMH/MDMH/DMH solution was prepared according to the procedure of Example 1. However, the amount of DMH added was adjusted so that the molar ratio of formaldehyde to DMH was 2:1.

Properties are summarized in Table 1.

Example 1, when compared with Comparative Example 1A, demonstrates that free formaldehyde content is kept below 0.1% by weight in aqueous DMDMH/MDMH/DMH solutions when the molar ratio of formaldehyde to DMH in the reaction is below 2:1 and particularly is 1.35:1.

Example 1 further demonstrates the effectiveness of the direct reaction of the present mixture in obtaining low free formaldehyde aqueous DMDMH/MDMH/DMH solutions with great stability.

TABLE 1

| Direct Reaction Production of Aqueous DMDMH/MDMH/DMH | | |
|---|---|---|
| Example | 1 | 1A |
| Molar Ratio Formaldehyde:DMH | 1.35:1 | 2:1 |
| Total Formaldehyde (%) (Initial/Six Months) | 12.4–12.6/12.3–13 | 13 |
| Free Formaldehyde (%) (Initial/Six Months) | 0.056–0.063/0.059–0.06 | 1 |
| $H_2O$ (%) (Initial/Six Months) | 46.5–47.3/43–48.2 | 59 |
| MeOH (%) (Initial/Six Months) | 0.12/— | — |
| DMH (%) (Initial/Six Months) | 3.5–3.8/— | 0 |
| MDMH (%) (Initial/Six Months) | 23.1–23.2/— | 7 |
| DMDMH (%) (Initial/Six Months) | 25.7–26.8/— | 33 |
| Solids (%) (Initial/Six Months) | 52.5/— | 40 |
| pH (Initial/Six Months) | 7.2–7.5/6.8–7.4 | — |

EXAMPLE 2

A 12 liter 3-necked round bottom flask equipped with a stirrer, a temperature regulator (Thermowatch ™ and heating mantle), and a condenser was charged with 4093 grams of formalin (37% aqueous formaldehyde, 12% methanol) (51 moles of formaldehyde) and 33 grams water. The pH was adjusted to 8.3 using aqueous sodium hydroxide. 4874 grams (38 moles) of DMH were added at room temperature in a molar ratio of formaldehyde to DMH of 1.35:1. An exotherm was observed, and the temperature increased to 45° C. After most of the DMH dissolved, the maximum temperature was reached, and the exotherm stopped. The pH was adjusted to 7 using aqueous sodium hydroxide. The reaction was heated at 55° C. for 3 hours and then was cooled to room temperature. The pH was adjusted to range from 6.8 to 7.2. 5 grams of filter aid (diatomaceous earth) were added, and the product was filtered.

Properties are summarized in Table 2.

This procedure was repeated four additional times with similar results.

TABLE 2

| Direct Reaction Production of Aqueous DMDMH/MDMH/DMH | |
|---|---|
| Example | 2 |
| Molar Ratio Formaldehyde:DMH | 1.35:1 |
| Total Formaldehyde (%) | 16.9 |
| Free Formaldehyde (%) | 0.04 |
| $H_2O$ (%) | 29.1 |
| MeOH (%) | 0.26 |
| DMH (%) | 5.3 |
| MDMH (%) | 31.8 |
| DMDMH (%) | 33.4 |
| Solids (%) | 70.6 |

EXAMPLE 3

A 12 liter 3-necked round bottom flask equipped with a stirrer, a temperature regulator (Thermowatch ™ and heating mantle), and a condenser was charged with 68.2 grams of formalin (37% formaldehyde, 1.2% methanol) (0.84 mole of formaldehyde) and 35.9 grams of water. The pH was adjusted to 8.3 using aqueous sodium hydroxide. 89.6 grams (0.7 mole) of DMH were added at room temperature in a molar ratio of formaldehyde to DMH of about 1.2:1. An exotherm was observed, and the temperature increased to 31° C. After most of the DMH dissolved, the maximum temperature was reached, and the exotherm stopped. The pH was adjusted with aqueous sodium hydroxide to 7. The reaction was heated at 55° C. for three hours and was then cooled to room temperature. The pH was then adjusted to a range of from 6.8 to 7.2. 5 grams of filter aid (diatomaceous earth) were added, and the product was filtered.

Properties are summarized in Table 3.

EXAMPLE 4

The procedure of Example 3 was followed except the amount of DMH (3840 grams) (30 moles) was adjusted so that the ratio of formaldehyde to DMH was 1.3:1.

Properties are summarized in Table 3.

The procedure was repeated four additional times with similar results.

EXAMPLE 5

The procedure of Example 3 was followed except the amount of DMH (3558 grams) (27.8 moles) was adjusted so that the ratio of formaldehyde to DMH was 1.4:1.

Properties are summarized in Table 3.

EXAMPLE 6

The procedure of Example 3 was followed except the amount of DMH (3328 grams) (26 moles) was adjusted so that the ratio of formaldehyde to DMH was 1.5:1.

Properties are summarized in Table 3.

COMPARATIVE EXAMPLE 6A

The procedure of Example 3 was followed except the amount of DMH (3017 grams) (23.7 moles) was adjusted so that the ratio of formaldehyde to DMH was 1.6:1.

Properties are summarized in Table 3.

Examples 2-6, when compared with Comparative Example 6A, demonstrate that formaldehyde to DMH molar ratios as low as 1.2 and up to 1.5 but less than 1.6, when used in the direct reaction method of the present invention, result in low formaldehyde aqueous DMDMH/MDMH/DMH solutions, while ratios of 1:6:1 do not.

TABLE 3

| Direct Reaction Production of Aqueous DMDMH/MDMH/DMH | | | | | |
|---|---|---|---|---|---|
| Example | 3 | 4 | 5 | 6 | 6A |
| Molar Ratio Formaldehyde:DMH | 1.2:1 | 1.3:1 | 1.4:1 | 1.5:1 | 1.6:1 |
| Total Formaldehyde (%) | 13.1 | 13 | 13 | 13 | 13 |
| Free Formaldehyde (%) | 0.04 | 0.048 | 0.071 | 0.086 | 0.13 |
| $H_2O$ (%) | 42.6 | 45.9 | 52.1 | 61.9 | 69 |
| DMH (%) | 5.7 | 7.8 | 5.9 | 3.2 | 2.9 |
| MDMH (%) | 29 | 11.8 | 11.8 | 8.4 | 7.6 |
| DMDMH (%) | 22.7 | 34.5 | 30.5 | 26.4 | 20.5 |
| Solids (%)[a] | 57.4 | 54.1 | 48.2 | 38.0 | 31 |

[a]Calculated

EXAMPLE 7

A 12 liter 3-necked round bottom flask equipped with a stirrer, a temperature regulator (Thermowatch TM and heating mantle), and a condenser was charged with 4093 grams of formalin (37% formaldehyde) (51 moles of formaldehyde) and 33 grams water. The pH was adjusted to 8.3 using aqueous sodium hydroxide. 4874 grams (38 moles) of DMH were added at room temperature in a molar ratio of formaldehyde to DMH of 1.34:1. An exotherm was observed, and the temperature increased to 45° C. After most of the DMH dissolved, the maximum temperature was reached, and the exotherm stopped. The pH was adjusted to 7 using aqueous sodium hydroxide. The reaction was heated at 55° C. for 3 hours and then was cooled to room temperature. The pH was adjusted to range from 6.8 to 7.2. 5 grams of filter aid (diatomaceous earth) were added, and the product was filtered. The product was then analyzed.

These procedures were repeated three additional times with similar results.

The product was then stored for six months at 25° C. and subsequently analyzed again.

Representative properties are summarized in Table 4.

EXAMPLE 8

The procedure of Example 7 was followed except the amount of DMH was adjusted so that the ratio of formaldehyde to DMH was 1.37:1.

Properties are summarized in Table 4.

Examples 7 and 8, when viewed in light of Examples 2 and 4, demonstrate that a molar ratio of formaldehyde to DMH of 1.35:1 gives lowest free formaldehyde content.

TABLE 4

| Direct Reaction Production of Aqueous DMDMH/MDMH/DMH | | |
|---|---|---|
| Example | 7 | 8 |
| Molar Ratio Formaldehyde:DMH | 1.34:1 | 1.37:1 |
| Total Formaldehyde (%) (Initial/Six Months) | 16.7-17/16-16.7 | 17 |
| Free Formaldehyde (%) (Initial/Six Months) | 0.04-0.047/0.043-0.048 | 0.055 |
| $H_2O$ (%) (Initial/Six Months) | 29.2-30.8/28.5-30.6 | — |
| DMH (%) (Initial/Six Months) | 4.6-5.5/4.7-5.3 | — |
| MDMH (%) (Initial/Six Months) | 31.1-31.8/30.5-31.8 | 24.1 |
| DMDMH (%) (Initial/Six Months) | 32.6-34.3/33.5-35.1 | — |
| pH (Initial/Six Months) | 7.1-7.34/7.03-7.24 | — |

EXAMPLE 9

A 500 ml 4-necked flask was charged with 128.1 grams (1 mole) of DMH, 42.8 grams (1.35 moles of para-formaldehyde) (95% formaldehyde), and 0.14 gram of sodium bicarbonate. The flask was rotated while it was heated in an oil bath at 105° C. The mixture changed from a free flowing solid blend to a flowable slurry and finally to a liquid in 55 minutes. The product was cooled to 25° C. to yield a highly viscous, substantially anhydrous liquid.

The product was analyzed and found to contain 24% total formaldehyde, 0.007% free formaldehyde, and 0.91% water.

EXAMPLE 10

36.3 grams of the product of Example 9 were dissolved in 14.5 grams of water. The product was analyzed and found to contain 17% total formaldehyde, 0.03% free formaldehyde, and 29.5% water.

EXAMPLE 11

37.2 grams of the product of Example 9 were dissolved in 32 grams of water. The product was analyzed and found to contain 12.7% total formaldehyde, 0.043% free formaldehyde, and 47.1% water.

Examples 9-11 demonstrate that substantially anhydrous methylolhydantoin can be prepared by the direct reaction method of the present invention. These substantially anhydrous compositions retain low free-formaldehyde properties when diluted with water.

The Post Addition Method

EXAMPLE 12

An aqueous solution of DMDMH, pH 7.2, having 13.5% by weight of total formaldehyde was prepared by charging a 250ml 3-necked flask with 76.5 parts of a 55% aqueous solution of DMDMH. 8.5 parts of water were added while mixing with a magnetic stir bar. 15 parts of solid DMH were added at room temperature, and stirring was continued until all of the solids were dissolved. The pH of the solution was 6.2 and was adjusted to 7 with aqueous sodium hydroxide. Any remaining solids were removed by filtration.

Properties are summarized in Table 5.

COMPARATIVE EXAMPLE 12A

An aqueous solution of DMDMH is prepared by mixing DMDMH powder and water to yield a 13% aqueous solution.

Properties are summarized in Table 5.

EXAMPLE 13

An aqueous DMDMH/MDMH/DMH solution was prepared by adding 17.5 parts of DMH to 85 parts of a concentrated DMDMH solution having 20.7% by weight total formaldehyde and 1.2% by weight free formaldehyde.

Properties are summarized in Table 5.

COMPARATIVE EXAMPLE 13A

An aqueous DMDMH/MDMH/DMH solution was prepared according to the procedure of Example 2. However, the amount of DMH added was adjusted so that the molar ratio of formaldehyde to DMH was 2:1 and the solids content was 55%.

Properties are summarized in Table 5.

Examples 12 and 13, when compared with Comparative Examples 12A and 13A respectively, demonstrate that post addition of DMH according to the present invention reduces the free formaldehyde content of aqueous DMDMH/MDMH solutions to below 0.1 percent.

TABLE 5

| | Post Addition of DMH | | | |
|---|---|---|---|---|
| | 12 | 12A | 13 | 13A |
| Total Formaldehyde (%) | 13.5 | 13 | 17.5 | 17.5 |
| Free Formaldehyde (%) | 0.03 | 1 | 0.024 | 1 |
| H$_2$O (%) | 42.2 | 59 | — | 44 |
| MeOH (%) | 0.16 | — | — | — |
| DMH (%) | 4.2 | 0 | 3.3 | 0 |
| MDMH (%) | 27.4 | 7 | 10 | 10 |
| DMDMH (%) | 26.1 | 33 | 25.3 | 45 |
| Solids (%) | 57.6 | 40 | 61.5 | 55 |

EXAMPLE 14

A mixture of 40 parts DMDMH powder, 50 parts water, and 10 parts of DMH was prepared.

Initially, free formaldehyde was determined to be 0.038% by weight, and after 45 days, free formaldehyde was determined to be 0.021% by weight.

Properties in summarized in Table 6.

COMPARATIVE EXAMPLE 14A

A mixture of 40 parts of DMDMH powder and 60 parts water was prepared. Free formaldehyde initially was determined to be 0.46% by weight, and after 57 days, free formaldehyde was determined to be 0.47% by weight.

Properties are summarized in Table 6.

EXAMPLE 15

A mixture of 40 parts of DMDMH powder, 45 parts water, and 15 parts of DMH was prepared.

Free formaldehyde initially was determined to be 0.009% by weight, and after 34 days, free formaldehyde was determined to be 0.019% by weight.

Properties are summarized in Table 6.

Examples 14 and 15, when compared with Comparative Example 14A, demonstrate the effectiveness of post addition of DMH in obtaining low free formaldehyde aqueous DMDMH/MDMH/DMH solutions with great stability.

TABLE 6

| Stability of Reaction Products of Post Addition Method | | | |
|---|---|---|---|
| | 14 | 14A | 15 |
| Methylolated-dimethylhydantoins | 40 | 40 | 40 |
| H$_2$O | 50 | 60 | 45 |
| DMH | 10 | — | 15 |
| Initial Free Formaldehyde (%) | 0.038 | 0.46 | 0.009 |
| Final Free-Formaldehyde (%/Days) | 0.021/45 | 0.47/57 | 0.019/34 |

COMPARATIVE EXAMPLE 16

A mixture of 90 parts of 55% by weight aqueous DMDMH having 1 to 1.5% by weight of free formaldehyde and 10% by weight of sodium bisulfite was prepared.

Initially, free formaldehyde was determined to be 0.01% by weight. However after 4 days, free formaldehyde levels rose to 0.13% by weight.

COMPARATIVE EXAMPLE 17

A mixture of 94 parts of 55% by weight aqueous DMDMH having 1 to 1.5% by weight of free formaldehyde and 6% by weight of ammonium carbonate was prepared.

Free formaldehyde was determined to be 0.56% by weight.

Comparative Examples 16 and 17 demonstrate that the addition of sodium bisulfite or ammonium carbonate does not reduce and maintain the free formaldehyde content of aqueous DMDMH solutions to below 0.1%.

Second DMH Addition

EXAMPLE 18

An aqueous DMDMH solution having approximately 20.7% by weight of total formaldehyde was prepared by charging a 250ml 3-necked round bottom flask equipped with a magnetic stir bar, a Thermowatch TM temperature controller, a glass stopper, and a condenser with 81.2 parts of formalin (37% formaldehyde). The pH was 3.6 and was adjusted to 8.18. A first DMH charge of 64.1 parts of DMH was added. An exotherm was observed, and the temperature rose to 43° C. The solution was then heated to 45° C. for three hours and subsequently was cooled to room temperature. An 11.5 part sample was removed.

A second DMH charge of 17.5 parts of DMH was added. The solution was stirred until the solids dissolved. The pH was 6.3 and was adjusted to 7 with aqueous sodium hydroxide. Any remaining solids were removed by filtration.

Properties are summarized in Table 7.

COMPARATIVE EXAMPLE 18A

The procedure of Examples 18 is followed except the second addition of DMH was deleted.

Properties are summarized in Table 7.

Example 18, when compared with Comparative Example 18A, demonstrates that post addition of DMH to DMDMH/MDMH solutions successfully lowers the free formaldehyde content to below 0.1%.

TABLE 7

| | Second DMH Addition | |
|---|---|---|
| Example | 18 | 18A |
| Total Formaldehyde (%) | 17.6 | 17.5 |
| Free Formaldehyde (%) | 0.07 | 1 |
| H$_2$O (%) | 29.9 | 44 |
| MeOH (%) | 0.19 | — |
| DMH (%) | 2.9 | 0 |
| MDMH (%) | 29.5 | 10 |
| DMDMH (%) | 37.1 | 45 |
| Solids (%) | 69.8 | 55 |

EXAMPLE 19

A stable aqueous solution of DMDMH/MDMH/DMH having a free formaldehyde content of 0.08% by weight was prepared by a direct reaction method. Subsequently, 3% by weight of DMH was added.

Free formaldehyde content was determined to be 0.051% by weight.

Example 19 demonstrates that post addition of DMH to aqueous DMDMH/MDMH/DMH solutions having a relatively low free formaldehyde content can be used to supplement a direct reaction method of preparation.

Biological Activity

The following biological procedures were used.

Procedure A

FD agar was prepared by dissolving 5 grams of beef extract, 5 grams of sodium chloride, 15 grams of agar, and 10 grams of anatone powder in 1 liter of distilled water. The mixture was heated with agitation, boiled for one minute, and subsequently sterilized at 121° C. for 20 minutes. It had a final pH of 7.

A 24 hour growth of the bacteria *Pseudomonas aeruginosa* (ATCC No. 9027) was prepared by transferring a loopful of a daily maintained stock culture to three fresh slants of FD agar. The inoculant was spread uniformly over the surface of the slant and was incubated for 24 hours at 37° C.

The culture was harvested by washing the surface of each slant with sterile saline and by placing the effluent into a sterile container. Additional saline was added to obtain a microbial count of approximately $1 \times 10^8$ colony forming units per ml of inoculum. This was determined by standardizing each inoculum spectrophotometrically.

Procedure B

The method of Procedure A was followed substituting the bacteria *Staphylococcus aureus* (ATCC No. 6538) for *Pseudomonas aeruginosa*.

Procedure C

The method of Procedure A was followed substituting the bacteria *Escherichia coli* (ATCC No. 8739) for *Pseudomonas aeruginosa*.

Procedure D

Potato dextrose agar was prepared by dissolving 39 grams of media in 1 liter of distilled water and bringing the solution to a boil. The mixture was dispensed into a 1000 ml flask. It was autoclaved for 20 minutes at 121° C., and then 35 to 40 ml were aseptically dispensed into sterile tissue culture flasks. Final pH was 5.6.

A seven day growth of the fungus *Aspergillus niger* (ATCC #16404) was prepared by transferring a loopful of a seven day maintained stock culture into a tissue culture flask containing fresh potato dextrose agar. The inoculant was spread uniformly over the surface and was incubated for seven days at 25° C.

A seven day culture was harvested by washing the surface of the tissue culture with sterile saline containing Triton X-100 (iso-octylphenoxypolyethoxyethanol), which had been previously prepared by dissolving 8.5 grams of reagent grade sodium chloride crystals in 1 liter of distilled water, adding 0.1 gram of Triton X-100, mixing thoroughly, and sterilizing at 121° C. for 20 minutes. The saline treated growth was loosened from the surface of the medium with sterile glass beads. The effluent was placed into a sterile tissue grinder and was macerated. The macerated inoculum was placed into a sterile container. Sufficient additional sterile saline was added to obtain a microbial count of approximately $1 \times 10^8$ colony forming units per ml of inoculum. This determination was made by an additional count of the inoculum using a Neubauer hemocytometer or a comparable chamber counting device.

Procedure E

Sabouraud dextrose agar was prepared by dissolving 65 grams of media into 1 liter of distilled water. The solution was heated with agitation and was boiled for one minute. The solution was sterilized at 121° C. for 20 minutes, and it had a final pH of 5.6.

A 48 hour growth of the yeast *Candida albicans* (ATCC #10231) was prepared by transferring a loopful of a 48 hour maintained stock culture to two slants of fresh sabouraud dextrose agar. The inoculant was spread uniformly over the slant surface and was incubated for 48 hours at 25° C.

The yeast was harvested by washing the surface with sterile saline and placing the effluent into a sterile container. The growth was loosened from the agar surface with a sterile loop. Sufficient additional saline to obtain a microbial count of approximately $1 \times 10^8$ colony forming units per ml of inoculum was added. This determination was made by a visual count of the inoculum using a Neubauer hemocytometer.

EXAMPLE 20

A 10.5% Neodol solution was prepared by mixing 450 grams of a polyethylene glycol ether of a mixture of synthetic $C_{12}$–$C_{15}$ fatty alcohols with an average of 12 to 15 moles of ethylene oxide (Neodol 25-12—Shell Chemical Co.) and 3825 grams of sterile water. 0.3% by weight of a stable aqueous DMDMH/MDMH/DMH solution having less than 0.06% by weight of free formaldehyde, at least 12.5% by weight of total formaldehyde, and 3.6% by weight of DMH, based upon 100% by weight of the solution, wherein the weight ratio of DMDMH to MDMH ranges from about 1:1.25 to about 3.5:1, prepared according to the method of Example 1, was added to the 10.5% Neodol solution.

Equal volumes of the microbial suspensions prepared by Procedures A, B, and C were mixed to yield a mixed bacterial suspension.

Equal volumes of the fungus and the yeast prepared by Procedures D and E, respectively, were mixed to yield a mixed fungal suspension.

40 ml of the DMDMH/MDMH/DMH-Neodol solution above were added to each of the mixed bacterial suspension and the mixed fungal suspension at a ratio of 0.1 ml of inoculum per 20 ml of DMDMH/MDMH/DMH-Neodol solution.

Inoculation was to result in a final microbial concentration of approximately $5 \times 10^6$ CFU/ml of material. The inoculated material was serially diluted by aseptically transferring 1 ml of the inoculated material to a sterile test tube containing 9 ml of a phosphate buffer and mixing thoroughly. This procedure was repeated until a dilution factor of $10^6$ was obtained.

Each dilution sample was plated by aseptically transferring 1 ml of each dilution to a sterile petri dish and then adding the appropriate medium. Trypticase soy agar with neutralizer, prepared by dissolving 24 grams of media and 25 ml of neutralizer stock solution in a 1 liter vessel, heating with agitation, boiling for 1 minute, and sterilizing at 121° C. for 20 minutes, was added to the bacterium plates. Sabouraud dextrose agar with neutralizer, prepared by dissolving 38 grams of media and 25 ml of neutralizer stock in a 1 liter vessel, heating with agitation, boiling for one minute, and sterilizing at 121° C. for 20 minutes, was added to the fungal plates. The bacteria plates were then incubated for 48 hours at 37° C., and the fungi plates were then incubated for 5 to 7 days at 25° C.

After each incubation, the growth for each test sample was quantitated and was recorded. Each test sample was quantitated at 0, 1, 3, 7, 14, 21 and 28 days of exposure time to the DMDMH/MDMH/DMH-Neodol preservative solution. The inoculated samples were stored at room temperature unless otherwise specified.

Results are illustrated in Table 8.

COMPARATIVE EXAMPLE 20A

The procedure of Example 20 was followed substituting 0.3% by weight of an aqueous solution of DMDMH having greater than 0.9% by weight of free formaldehyde and 12% by weight of total formaldehyde for the DMDMH.

Results are illustrated in Table 8.

EXAMPLE 21

The procedure of Example 20 was followed substituting 0.5% by weight of the aqueous solution of DMDMH/MDMH/DMH prepared by the method of Example 1 for the DMDMH/MDMH/DMH. Results are illustrated in Table 8.

COMPARATIVE EXAMPLE 21A

The procedure of Example 20A was followed substituting 0.5% by weight of the aqueous solution of DMDMH/MDMH/DMH for the DMDMH/MDMH/DMH.

Results are illustrated in Table 8.

EXAMPLE 22

The procedure of Example 20 was followed substituting 0.2% by weight of an aqueous solution of DMDMH/MDMH/DMH prepared by the method of Example 2 for the DMDMH/MDMH/DMH.

Results are illustrated in Table 8.

EXAMPLE 23

The procedure of Example 22 was followed substituting a 0.4% by weight of the aqueous solution of DMDMH/MDMH/DMH for the DMDMH/MDMH/DMH.

Results are illustrated in Table 8.

COMPARATIVE EXAMPLE 23A

The procedure of Example 20 was followed except no aqueous DMDMH/MDMH/DMH solution was added to the 10% Neodol solution.

Results are illustrated in Table 8.

TABLE 8

| | Aqueous DMDMH/MDMH/DMH and 10% Neodol Solution | | | | | | |
|---|---|---|---|---|---|---|---|
| Example | 20 | 20A | 21 | 21A | 22 | 23 | 23A |
| | Mixed Bacterial Inoculum (CFU/ml) | | | | | | |
| Day 0 | 7.6E + 6 | 6.7E + 6 | 5.2E + 6 | 3.6E + 6 | 5.3E + 6 | 4.1E + 6 | 1E + 7 |
| Day 1 | 9E + 5 | 1E + 6 | 4E + 5 | 6E + 5 | 1E + 6 | 6E + 5 | 9E + 6 |
| Day 3 | 3.7E + 4 | 7E + 3 | 8E + 3 | 1.3E + 2 | 7E + 4 | 1.6E + 4 | 8E + 6 |
| Day 7 | <10 | <10 | <10 | <10 | <10 | <10 | 7E + 6 |
| Day 28 | <10 | <10 | <10 | <10 | <10 | <10 | 4.8E + 6 |
| | Mixed Fungal Inoculum (CFU/ml) | | | | | | |
| Day 0 | 1E + 6 | 4E + 5 | 4E + 5 | 3E + 5 | 3E + 5 | 6E + 5 | 4E + 5 |
| Day 1 | 3E + 5 | 4E + 5 | 5E + 3 | 2E + 4 | 1.7E + 5 | 1E + 5 | 9E + 5 |
| Day 3 | 6E + 4 | 7E + 4 | 9E + 4 | 9E + 3 | 7E + 4 | 7E + 4 | 9E + 4 |
| Day 7 | 5E + 3 | 3E + 4 | 1E + 3 | 1E + 4 | 2.4E + 4 | 3E + 4 | 4E + 4 |
| Day 28 | 3.8E + 5 | 2.1E + 5 | 1.1E + 5 | 1.1E + 5 | 4.5E + 5 | 1.5E + 5 | 5.9E + 5 |

EXAMPLE 24

The procedure of Example 20 was followed, substituting a 10.5% by weight sodium lauryl ether sulfate solution prepared by mixing 450 grams of a sodium salt of sulfated, ethoxylated lauryl alcohol $CH_3(CH_2)_{10}CH_2(OCH_2CH_2)_nOSO_3Na$ (N=1–4) and 3825 ml of sterile water, for the 10.5% Neodol solution.

Results are illustrated in Table 9.

COMPARATIVE EXAMPLE 24A

The procedure of Comparative Example 20A was followed, substituting a 10.5% by weight sodium lauryl ether sulfate solution prepared according to the procedure of Example 24 for the 10.5% Neodol solution.

Results are illustrated in Table 9.

EXAMPLE 25

The procedure of Example 21 was followed, substituting a 10.5% by weight sodium lauryl ether sulfate solution prepared according to the procedure of Example 24 for the 10.5% Neodol solution.

Results are illustrated in Table 9.

COMPARATIVE EXAMPLE 25A

The procedure of Comparative Example 21A was followed, by substituting a 10.5% by weight sodium lauryl ether sulfate solution prepared according to the procedure of Example 24 for the 10.5% Neodol solution.
Results are illustrated in Table 9.

EXAMPLE 26

The procedure of Example 22 was followed, substituting a 10.5% by weight sodium lauryl ether sulfate solution prepared according to the procedure of Example 24 for the 10.5% Neodol solution.
Results are illustrated in Table 9.

EXAMPLE 27

The procedure of Example 23 was followed, substituting a 10.5% by weight sodium lauryl ether sulfate solution prepared according to the procedure of Example 24 for the 10.5% Neodol solution.
Results are illustrated in Table 9.

COMPARATIVE EXAMPLE 27A

The procedure of Comparative Example 23A was followed, substituting a 10.5% by weight sodium lauryl ether sulfate solution prepared according to the procedure of Example 24 for the 10.5% Neodol solution.
Results are illustrated in Table 9.

COMPARATIVE EXAMPLE 29A

The procedure of Comparative Example 21A was followed, substituting a liquid dishwasher detergent solution prepared according to the procedure of Example 28 for the 10.5% Neodol solution.
Results are illustrated in Table 10.

EXAMPLE 30

The procedure of Example 22 was followed, substituting a liquid dishwasher detergent solution prepared according to the procedure of Example 28 for the 10.5% Neodol solution.
Results are illustrated in Table 10.

EXAMPLE 31

The procedure of Example 23 was followed, substituting a liquid dishwasher detergent solution prepared according to the procedure of Example 28 for the 10.5% Neodol solution.
Results are illustrated in Table 10.

TABLE 9

| Aqueous DMDMH/MDMH/DMH and 10% Sodium Laurethsulfate Solution | | | | | | | |
|---|---|---|---|---|---|---|---|
| Example | 24 | 24A | 25 | 25A | 26 | 27 | 27A |
| Mixed Bacterial Inoculum (CFU/ml) | | | | | | | |
| Day 0 | 9.4E + 6 | 6.5E + 6 | 1E + 7 | 3.4E + 6 | 4.7E + 6 | 6.2E + 6 | 1E + 7 |
| Day 1 | 3.5E + 4 | 7.5E + 2 | 1.4E + 3 | <10 | 1E + 5 | 1E + 4 | 8E + 6 |
| Day 3 | <10 | <10 | <10 | <10 | <10 | <10 | 3E + 5 |
| Day 7 | <10 | <10 | <10 | <10 | <10 | <10 | 8E + 5 |
| Day 28 | <10 | <10 | <10 | <10 | <10 | <10 | 1.7E + 6 |
| Mixed Fungal Inoculum (CFU/ml) | | | | | | | |
| Day 0 | 5E + 5 | 6E + 5 | 3E + 5 | 4E + 5 | 5E + 5 | 3E + 5 | 3E + 5 |
| Day 1 | 9E + 3 | 3.7E + 2 | 1.3E + 2 | 2E + 1 | 1E + 2 | 3E + 1 | 1E + 5 |
| Day 3 | <10 | <10 | <10 | <10 | <10 | <10 | 5E + 4 |
| Day 7 | <10 | <10 | <10 | <10 | <10 | <10 | 9E + 4 |
| Day 28 | <10 | <10 | <10 | <10 | <10 | <10 | 9E + 4 |

EXAMPLE 28

The procedure of Example 20 was followed, substituting a liquid dishwater detergent solution prepared by mixing 2700 grams of sterile water, 67.5 grams of sodium hydroxide pellets, 540 grams of dodecylbenzene sulfuric acid (Stepan BDA 96%), 99 grams of 1:1 lauric diethanolamide (Carsonol®SAL-9), 472.5 grams of sodium lauryl ether sulfate, 45 grams of Polysorbate 20 (mixture of laurate esters of sorbitol and sorbitol anhydride with about 20 moles of ethylene oxide), 45 grams of Ethanol SDA-3A, 21 grams of 0.1% sodium hydroxide, and an additional 285 grams of sterile water, for the 10.5% Neodol solution.
Results are illustrated in Table 10.

COMPARATIVE EXAMPLE 28A

The procedure of Comparative Example 20A was followed, substituting a liquid dishwasher detergent solution prepared according to the procedure of Example 28 for the 10.5% Neodol solution.
Results are illustrated in Table 10.

EXAMPLE 29

The procedure of Example 21 was followed, substituting a liquid dishwasher detergent solution prepared according to the procedure of Example 28 for the 10.5% Neodol solution.

COMPARATIVE EXAMPLE 31A

The procedure of Comparative Example 23A was followed, substituting a liquid dishwasher detergent solution prepared according to the procedure of Example 28 for the 10.5% Neodol solution.
Results are illustrated in Table 10.

Examples 20–31 illustrate that aqueous DMDMH/MDMH/DMH solutions within the scope of the present invention having less than 0.1% free formaldehyde eliminated the mixed bacterial contamination after seven days exposure in all test materials and eliminated the mixed fungal contamination after seven days of exposure in all test materials except the 10.5% Neodol solution.

Comparative Examples 20A, 21A, 24A, 25A, 28A and 29A illustrate that aqueous DMDMH solutions with greater than 1% free formaldehyde completely eliminated the mixed bacterial contamination after seven days of exposure in all test materials. The mixed fungal contamination was completely eliminated after seven days of exposure in all test materials at high total formaldehyde concentration and in all test materials except 10% Neodol at lower total formaldehyde concentrations.

Therefore, it is demonstrated that low free formaldehyde compositions of the present invention are as effective as high free formaldehyde compositions of the prior art.

TABLE 10

| Aqueous DMDMH/MDMH/DMH and Liquid Dishwasher Detergent | | | | | | | |
|---|---|---|---|---|---|---|---|
| Example | 28 | 28A | 29 | 29A | 30 | 31 | 31A |
| Mixed Bacterial Inoculum (CFU/ml) | | | | | | | |
| Day 0 | 2.3E + 6 | 1.3E + 6 | 4E + 6 | 5.2E + 6 | 4.2E + 6 | 2.9E + 6 | 1.3E + 7 |
| Day 1 | <10 | <10 | <10 | <10 | 3E + 1 | <10 | 1E + 7 |
| Day 3 | <10 | <10 | <10 | <10 | <10 | <10 | 4.9E + 6 |
| Day 7 | <10 | <10 | <10 | <10 | <10 | <10 | 4E + 6 |
| Day 28 | <10 | <10 | <10 | <10 | <10 | <10 | 3.2E + 5 |
| Mixed Fungal Inoculum (CFU/ml) | | | | | | | |
| Day 0 | 3E + 5 | 3E + 5 | 1E + 5 | 1E + 5 | 1E + 5 | 3E + 5 | 3E + 5 |
| Day 1 | <10 | 9E + 1 | <10 | 3E + 1 | 3E + 2 | <10 | 9E + 4 |
| Day 3 | <10 | <10 | <10 | <10 | <10 | <10 | 1E + 5 |
| Day 7 | <10 | <10 | <10 | <10 | <10 | <10 | 8E + 5 |
| Day 28 | <10 | <10 | <10 | <10 | <10 | <10 | 6E + 4 |

All patents, applications, and test methods mentioned above are hereby incorporated by reference.

Many variations of the present invention will suggest themselves to those skilled in the art in light of the above detailed description. Such obvious variations are within the full intended scope of the appended claims.

What is claimed is:

1. An aqueous solution comprising: (a) 20 to 40 wt. % of dimethyloldimethylhydantoin, (b) monomethyloldimethylhydantoin, and (c) dimethylhydantoin in a weight ratio of dimethyloldimethylhydantoin to monomethyloldimethylhydantoin of from about 1:2.25 to 3.5:1; said solution having a total formaldehyde content of from 10 to 25 wt. % and a free formaldehyde content of less than 0.1%.

2. The aqueous solution of claim 1 wherein said solution has from about 2 to 6% by weight of dimethylhydantoin based upon 100% by weight of said composition.

3. The aqueous solution of claim 1 wherein said solution has from about 10 to 18% by weight of total formaldehyde.

4. The aqueous solution of claim 1 wherein said solution has from about 12 to 17% by weight of total formaldehyde.

5. The aqueous solution of claim 1, having about 12% by weight of total formaldehyde.

6. The aqueous solution of claim 1, having about 17% by weight of total formaldehyde.

7. The aqueous solution of claim 1 wherein said solution comprises from about 25 to 35% by weight of dimethyloldimethylhydantoin based on 100% by weight of total composition.

8. A substantially anhydrous composition comprising (a) dimethyloldimethylhydantoin, (b) monomethyloldimethylhydantoin, and (c) dimethylhydantoin in a weight ratio of dimethyloldimethylhydantoin to monomethyloldimethylhydantoin of from about 1:1.25 to 3.5:1.

9. A method of retarding the microbial growth in a liquid medium susceptible to said growth comprising mixing a biocidal effective amount of a composition as defined in claim 1 with said medium.

10. A method as defined in claim 9, wherein said liquid medium is selected from the group consisting of a personal care product, a cosmetic product, an industrial product, and a household product.

11. A composition comprising a liquid medium susceptible to microbial growth and a biocidal effective amount of a composition as defined in claim 1.

12. A composition as defined in claim 11, wherein said liquid medium is selected from the group consisting of a personal care product, a cosmetic product, an industrial product, and a household product.

* * * * *

UNITED STATES PATENT AND TRADEMARK OFFICE
CERTIFICATE OF CORRECTION

PATENT NO. : 5,405,862
DATED : April 11, 1995
INVENTOR(S) : Thomas E. FARINA and Marvin ROSEN

It is certified that error appears in the above-indentified patent and that said Letters Patent is hereby corrected as shown below:

Claim 1, column 17, line 34, change "1:2:25" to --1:1.25--

Signed and Sealed this

Fifteenth Day of July, 1997

Attest:

BRUCE LEHMAN

Attesting Officer    Commissioner of Patents and Trademarks